(12) United States Patent
Otsubo et al.

(10) Patent No.: US 6,761,712 B2
(45) Date of Patent: Jul. 13, 2004

(54) DISPOSABLE PANTS OF TRUNKS-TYPE

(75) Inventors: Toshifumi Otsubo, Kagawa-ken (JP); Hiroki Yamamoto, Kagawa-ken (JP)

(73) Assignee: Uni-Charm Corporation, Kawanoe (JP)

(*) Notice: Subject to any disclaimer, the term of this patent is extended or adjusted under 35 U.S.C. 154(b) by 0 days.

(21) Appl. No.: 09/878,243

(22) Filed: Jun. 12, 2001

(65) Prior Publication Data

US 2002/0082578 A1 Jun. 27, 2002

(30) Foreign Application Priority Data

Jun. 30, 2000 (JP) ........................................ 2000-199025

(51) Int. Cl.[7] ................................................. A61F 13/15
(52) U.S. Cl. .................... 604/396; 604/394; 604/385.01
(58) Field of Search ................................. 604/394, 395, 604/396, 397; 2/400, 403, 405

(56) References Cited

U.S. PATENT DOCUMENTS

| | | | |
|---|---|---|---|
| 1,504,361 A | | 8/1924 | McLoughlin |
| 1,842,472 A | * | 1/1932 | Firsching, Jr. |
| 3,613,687 A | * | 10/1971 | Kennedy .................... 604/396 |
| 4,555,245 A | * | 11/1985 | Armbruster ................. 604/396 |
| 5,210,882 A | * | 5/1993 | Moretz et al. ................. 2/404 |
| 5,274,854 A | * | 1/1994 | Wenner et al. ................. 2/403 |
| 5,435,014 A | * | 7/1995 | Moretz et al. ................. 2/403 |
| 5,555,568 A | * | 9/1996 | Yon ................................. 9/96 |
| 5,669,902 A | * | 9/1997 | Sivilich ....................... 604/396 |
| 5,690,626 A | | 11/1997 | Suzuki et al. |
| 5,716,350 A | * | 2/1998 | Ryan ........................ 604/385.1 |
| 6,018,822 A | * | 2/2000 | Hernandez ..................... 2/405 |
| 6,061,839 A | * | 5/2000 | Smolik .......................... 2/400 |

FOREIGN PATENT DOCUMENTS

| | | |
|---|---|---|
| CA | 2320256 | 6/2000 |
| JP | 6-57501 | 3/1994 |
| JP | 6-63073 | 3/1994 |

* cited by examiner

Primary Examiner—Weilun Lo
Assistant Examiner—Jacqueline F Stephens
(74) Attorney, Agent, or Firm—Lowe Hauptman Gilman & Berner LLP

(57) ABSTRACT

Here is disclosed disposable pants of trunks-type having a pair of lateral trunk regions and a middle trunk region wherein each of the lateral trunk regions has an upper section and a lower section while the middle trunk region has a front trunk section, a rear trunk section, a crotch section and a pair of downward extensions so that the front and rear trunk sections and the crotch section extend so as to intersect the upper sections while the downward extensions extend in parallel to the lower sections and wherein the upper sections and the front and rear trunk sections are bonded together along edges thereof except upper edges thereof forming a waist-opening while the lower sections and the downward extensions are bonded together along edges thereof except lower edges forming a pair of leg-openings.

13 Claims, 7 Drawing Sheets

DISPOSABLE PANTS OF TRUNKS-TYPE

BACKGROUND OF THE INVENTION

This invention relates to a disposable pants of trunks-type.

The disposable pants of trunks-type formed by placing front and rear waist regions prepared separately of each other and bonding these front and rear waist regions along a bonding line formed in a crotch regions of the these front and rear waist regions so as to describe a curve convex toward a waist line is well known, for example, from disclosures of Japanese Patent Application Publication Nos. 1994-57501A and 1994-63073A. These pants of prior art are formed at the top with a waist-opening and at the bottom with a pair of leg-openings. The bonding line formed in the crotch region to describe the curve convex toward the waist line enables an actual width of the crotch region to be enlarged and thereby provides a sufficient area adapted to cover the inner sides of wearer's thighs.

The pants disclosed in these Publication comprise the front and rear waist regions of which the sheet surfaces put flat together and the interior of the pants should be expanded to form a space adapted to enclose the wearer's belly, hip and thighs.

SUMMARY OF THE INVENTION

It is an object of this invention to provide a disposable pants of trunks-type having its interior previously formed with a space adapted to enclose belly and hip of a wearer.

According to this invention, there is provided a disposable pants of trunks-type having an upper edge defining a waist-opening and a lower edge defining a pair of leg-openings. openings.

The improvement according to this invention is in that the pants comprises: a pair of lateral trunk regions opposed to each other in a plane-symmetry relationship and a middle waist region extending between the lateral trunk regions so as to be convex downward wherein each of the lateral trunk regions has an upper section and a lower section extending downward from the upper section while the middle trunk region has a front trunk section, a rear trunk section opposed to the front trunk section, a crotch section extending between the front and rear trunk sections and a pair of downward extensions extending downward from transversely opposite side edges of the crotch section so that the front and rear trunk sections and the crotch section extend so as to intersect the upper sections while the downward extensions extend in parallel to the lower sections and the upper sections and the front and rear trunk sections are bonded together along edges thereof except upper edges thereof forming the waist-opening while the lower sections and the downward extensions are bonded together along edges thereof except lower edges forming a pair of leg-openings.

According to one preferred embodiment of this invention, an absorbent member adapted to absorb and to hold excretion prepared separately of the pants lies on an inner side of the middle trunk region and attached to the front trunk section and the crotch section, at least to the crotch section and wherein the absorbent member comprises a liquid-pervious topsheet, a liquid-impervious backsheet and a liquid-absorbent core disposed between these two sheets.

According to another preferred embodiment of this invention, the lateral trunk regions and the middle trunk region, at least the middle trunk region comprises a liquid-pervious topsheet, a liquid-impervious backsheet and a liquid-absorbent core disposed between these two sheets.

DETAILED DESCRIPTION OF THE PREFERRED EMBODIMENTS

Details of the disposable pants of trunks-type according to this invention will be more fully understood from the description given hereunder with reference to the accompanying drawings.

Figure 1:
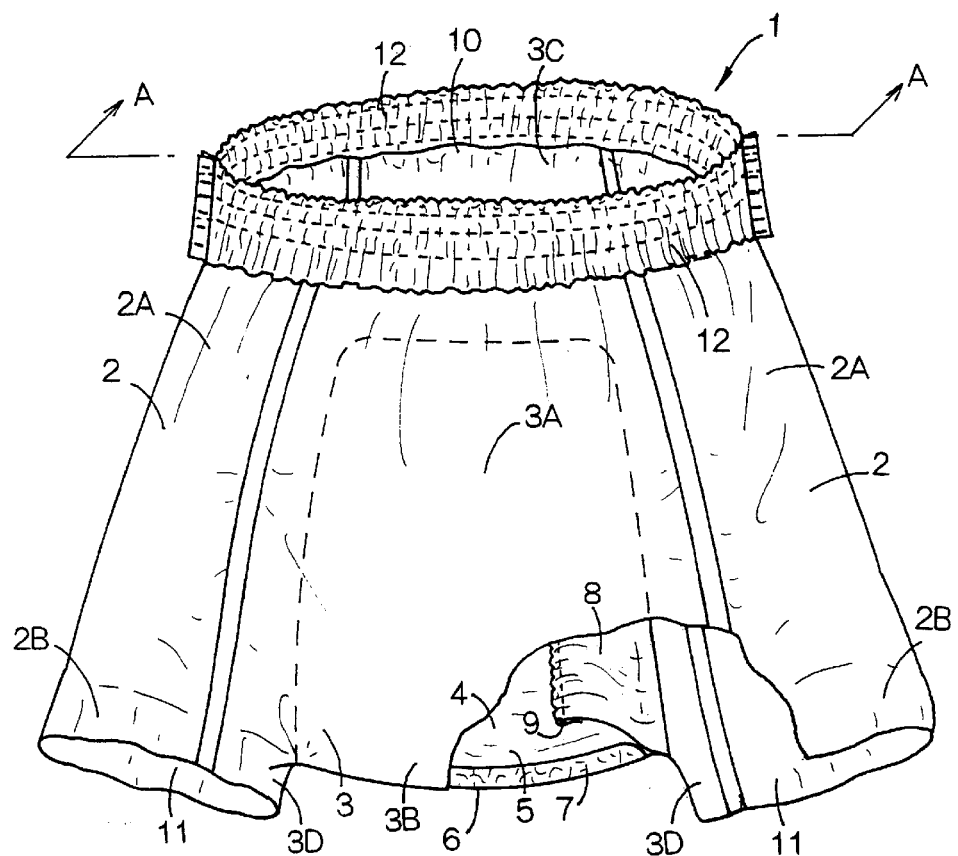
FIG. 1 is a perspective view showing pants as partially broken away.
Figure 2:
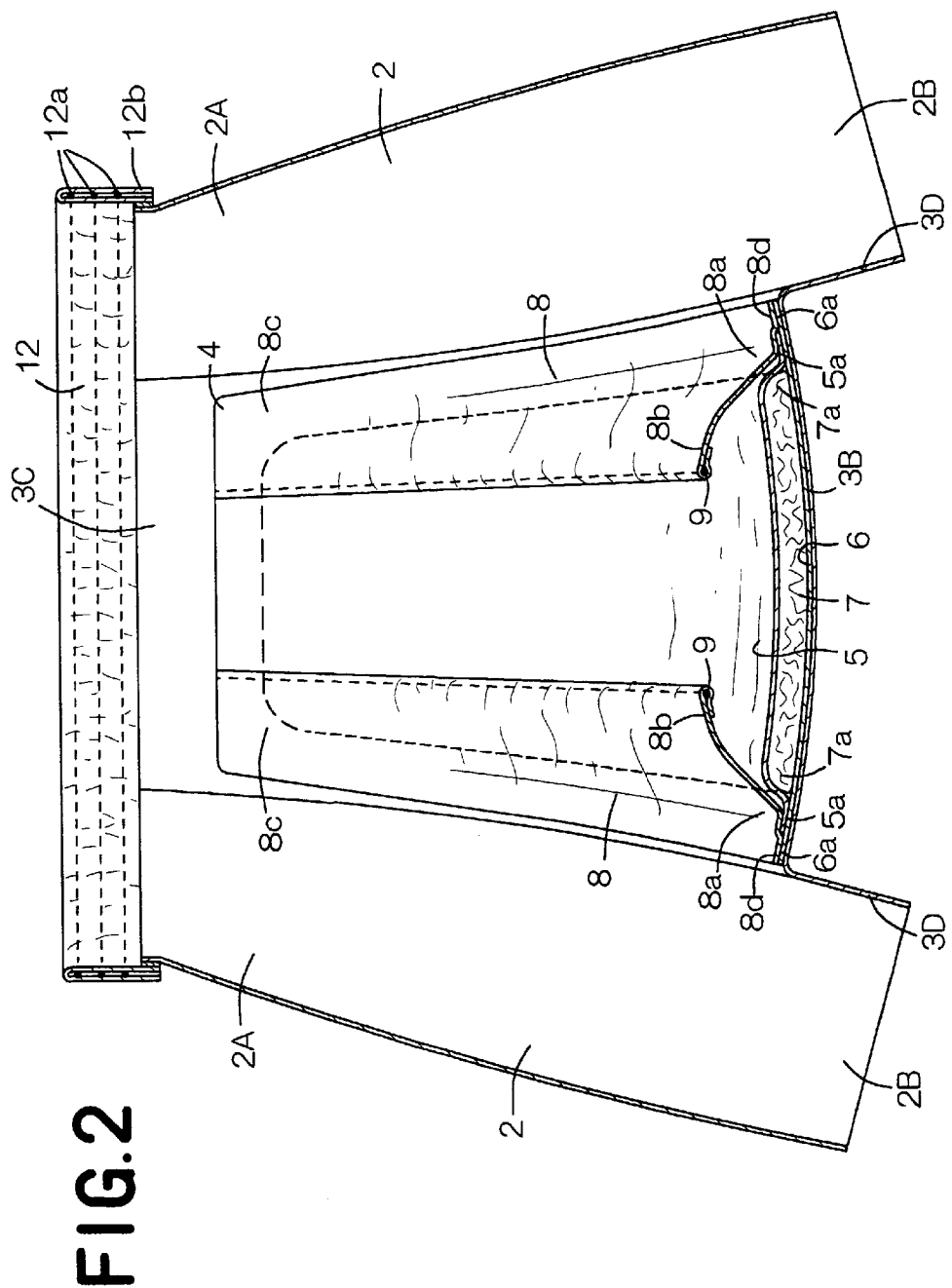
FIG. 2 is a sectional view taken along a line A—A in FIG. 1.
Figure 3:
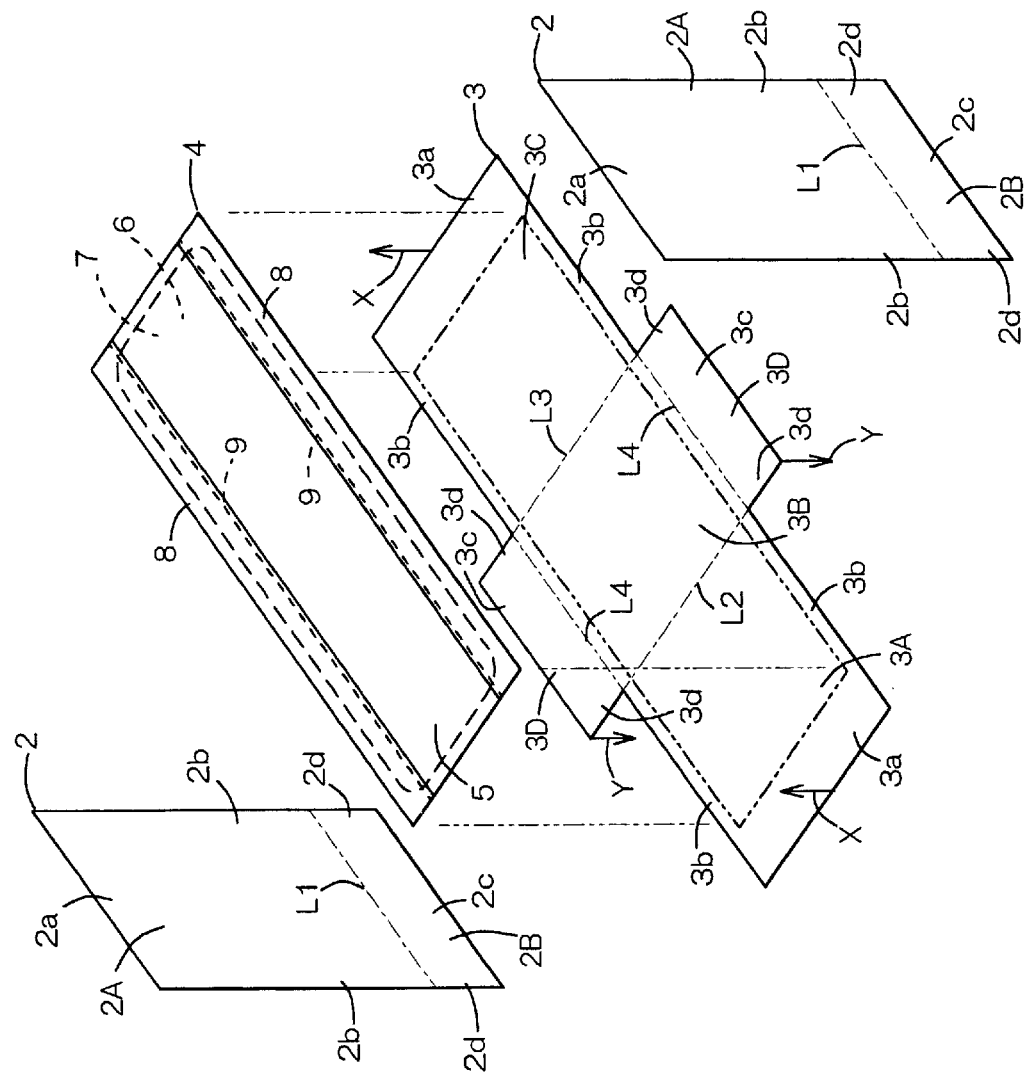
FIG. 3 is an exploded perspective view showing the pants of FIG. 1.
Figure 4:
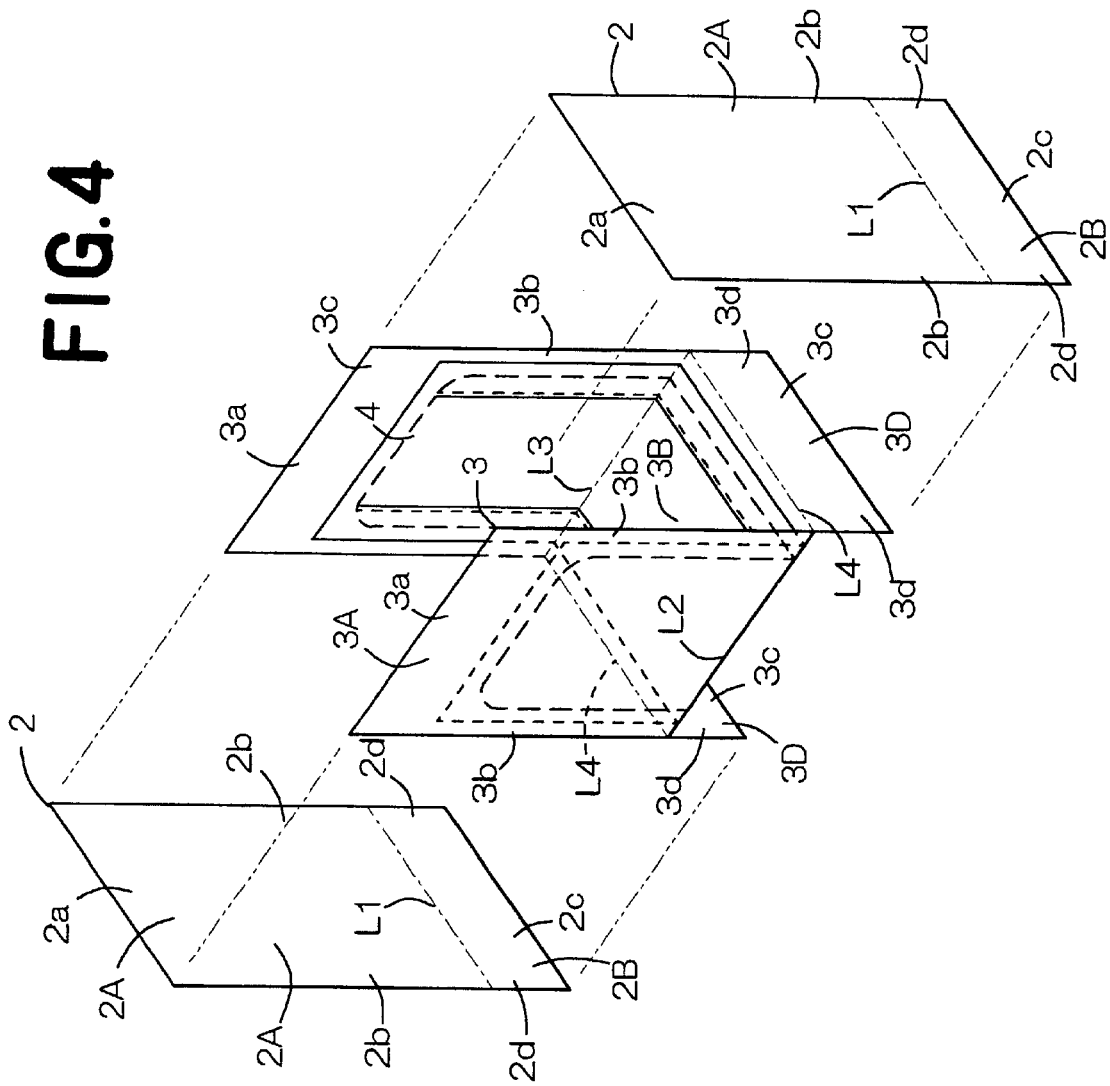
FIG. 4 is an exploded perspective view showing the pants of FIG. 1.

FIG. 1 a perspective view showing pants 1 as partially broken away and FIG. 2 is a sectional view taken along a line A—A in FIG. 1. FIGS. 3 and 4 are exploded perspective views showing the pants 1 of FIG. 1 with an elastic band 12 as will be described later being eliminated. Referring to FIGS. 3 and 4, the respective lateral trunk regions 2 are positioned in a plane-symmetric relationship and, between the regions 2, a middle trunk region 3 and an absorbent member 4 adapted to absorb and to hold excretion are laid. Referring again to FIGS. 3 and 4, single-dot-chain lines L1, L2, L3 and L4 respectively indicate border lines as follow: L1 indicates the border line dividing each of the lateral trunk regions 2 into upper and lower sections 2A, 2B respect to a crotch region 3B; L2 indicates the border line dividing the middle trunk region 3 into front and rear trunk sections 3A, 3C and the crotch section 3B; L3 indicates the border line dividing the middle trunk regions 3 into a rear trunk section 3C and the crotch section 3B; and L4 indicates the border line defining the crotch section 3B from its downward extension 3D.

The pants 1 are composed of a pair of the lateral trunk regions 2 transversely opposed to each other in a plane-symmetry relationship, the middle trunk region 3 and the absorbent member 4 prepared separately of the pants 1. The pants 1 include a waist-opening defining an upper end of the pants 1 and a pair of leg-openings 11 defining a lower end of the pants 1. The absorbent member 4 is attached to the inner side of the middle trunk region 3. The waist-opening 10 is provided along its peripheral edge with the elastically stretchable band 12 comprising a plurality of elastically stretchable members 12a and a nonwoven fabric 12b. These elastic members 12a are covered with the nonwoven fabric 12b and bonded under tension to the nonwoven fabric 12b.

Each of the lateral trunk regions 2 is formed with an elastically stretchable nonwoven fabric and comprises the upper section 2A and the lower sections 2B extending downward from the upper section 2A beyond the crotch section 3B. The upper section 2A has an upper edge 2a defining the waist-opening 10 and transversely opposite side edges 2b extending in parallel to each other. The lower section 2B has a lower edge 2c defining each of the leg-openings 11 and transversely opposite side edges 2d.

The middle waist region 3 is formed with an elastically stretchable nonwoven fabric and has the front trunk section 3A, the rear trunk section 3C, the crotch section 3B extending between the front and rear trunk sections 3A, 3C and a pair of the downward extensions 3D extending downward from both sides of the crotch section 3B.

Each of the front and rear trunk sections 3A, 3C has an upper edge 3a defining the waist-opening 10 and transversely opposite side edges 3b extending in parallel to each other.

Each of the downward extension 3D has a lower edge 3c defining each of the leg-openings 11 and transversely opposite side edges 3d extending in parallel to each other.

The absorbent member 4 lies between the front and rear trunk sections 3A, 3C and the crotch section 3B of the middle trunk region 3. The absorbent member 4 comprises a liquid-pervious topsheet 5, a liquid-impervious backsheet 6 opposed to the inner surface of the middle trunk region 3 and a liquid-absorbent core 7 disposed between these sheets 5, 6. Both the topsheet 5 and the backsheet 6 are non-stretchable. The core 7 has its entire surface covered with water-pervious tissue paper (not shown) via which the core 7 is bonded to the topsheet 5 and/or the backsheet 6. The absorbent member 4 includes a pair of side sheets 8 attached to transversely opposite side edges 7a of the core 7 so as to extend outward beyond the side edges 7a. In the absorbent member 4, the backsheet 6 is intermittently bonded to the inner surface of the middle trunk region 3.

Each of the side sheets 8 is non-stretchable and has an outer side edge portion 8a fixed to the topsheet 5, a deformable inner side edge portion 8b extending in parallel to the outer side edge portion 8a and longitudinally opposite end portions 8c collapsed onto the inner side of the member 4 and fixed to the topsheet 5 in this collapsed state. The outer side edge portion 8a includes a portion 8d extending outward beyond the side edge 7a of the core 7. The inner side edge portion 8b is folded back so as to wrap an elastic member 9 which is bonded under tension to the inner side edge portion 8b. The inner side edge portion 8b rises on the topsheet 5 as this elastic member 9 contracts.

In the absorbent member 4, the transversely opposite side edges 5a of the topsheet 5 extend outward slightly beyond the transversely opposite side edges 7a of the core 7 while the transversely opposite side edges 6a of the backsheet 6 as well as the outer side edge portions 8d of the respective side sheets 8 extend further outward beyond the transversely opposite side edges 5a of the topsheet 5. The transversely opposite side edge portions 5a are disposed between the transversely opposite side edge portions 6a and the transversely opposite side edge portions 8d and fixed to the portions 6a and/or the portions 8d. The transversely opposite side edge portions 6a and the transversely opposite side edge portions 8d are put flat and bonded together.

Now the procedure for making the pants 1 will be described with reference to the exploded perspective view of FIG. 3. Referring to FIG. 3, the downward extensions 3D rectilinearly extend from the crotch section 3B.

First, the absorbent member 4 is placed upon and bonded to the inner surface of the middle trunk region 3. Then, the front trunk section 3A and the rear trunk section 3C are folded upward along the chain lines L2, L3 in a direction indicated by an arrow X substantially at a right angle with respect to the crotch section 3B and the downward extensions 3D of the middle trunk region 3 are folded downward along the chain lines L4 in a direction indicated by an arrow Y substantially at a right angle with respect to the crotch section 3B. After the middle trunk region 3 has been folded in this manner, the front and rear trunk sections 3A, 3C face each other and the downward extensions 3D extend downward from the crotch section 3B, as will be seen in FIG. 4.

Referring to FIG. 4, the respective side edge potions 2b, 3b of the respective lateral trunk regions' upper sections 2A are placed upon the respective side edge portions 3b of the front and rear trunk sections 3A, 3C while the respective side edge portions 2d of the respective lower sections 2B are placed upon the respective side edge portions 3d of the respective downward extensions 3D. Then, the side edge portions 2b may be bonded to the side edge portions 3b while the side edge portions 2d may be bonded to the side edge portions 3d to obtain the pants 1 of FIG. 1.

In the pants 1 assembled in this manner, the front and rear trunk sections 3A, 3C and the crotch section 3B of the middle trunk region 3 extend so as to intersect the respective upper sections 2A of the lateral trunk regions 2 while the downward extensions 3D of the middle trunk region 3 extend in parallel to the respective lower sections 2B of the lateral trunk regions 2. Thus, the pants 1 is distinguished from the pants of prior art having sheet surfaces of its front and rear trunk regions placed upon each other in that the front and rear trunk sections 3A, 3C extend so as to intersect the crotch section 3B so that the upper sections 2A, the front and rear trunk sections 3A, 3C and the crotch section 3B define a space within the pants 1.

Figure 5:
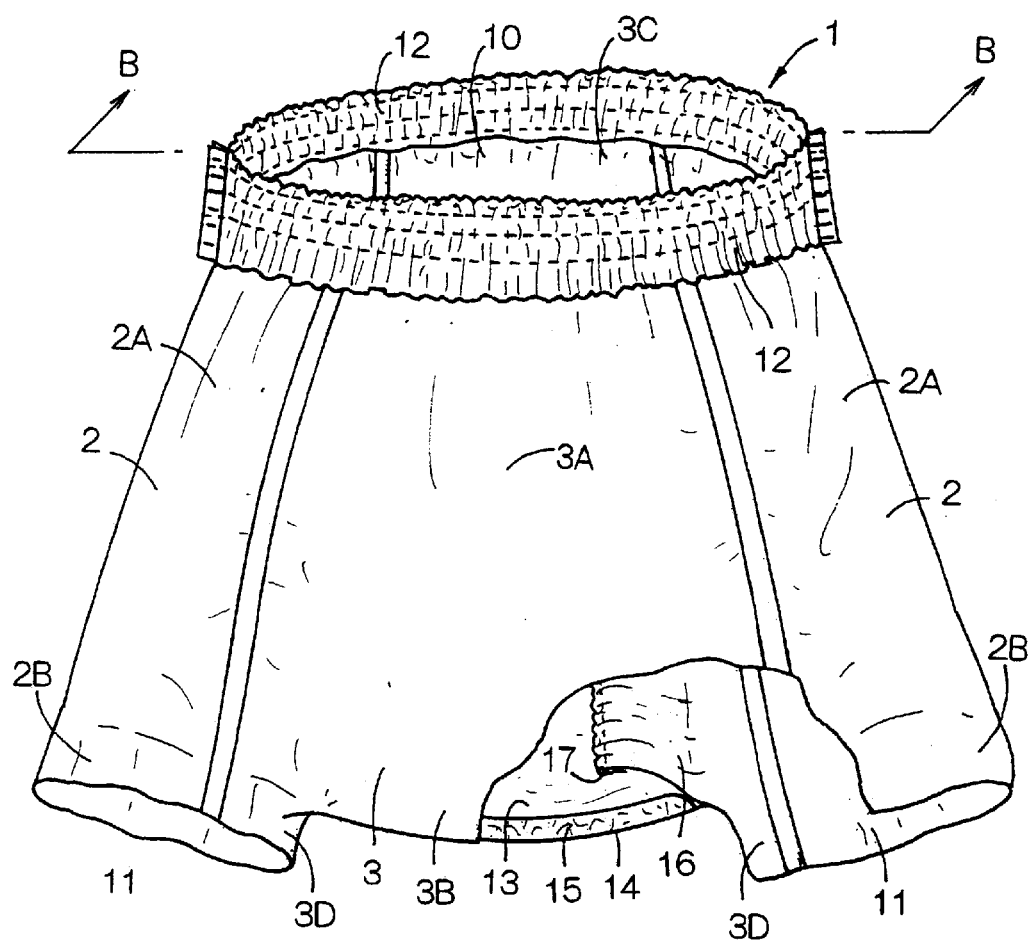
FIG. 5 is a view similar to FIG. 1 but showing an alternative embodiment of the pants as partially broken away.
Figure 6:
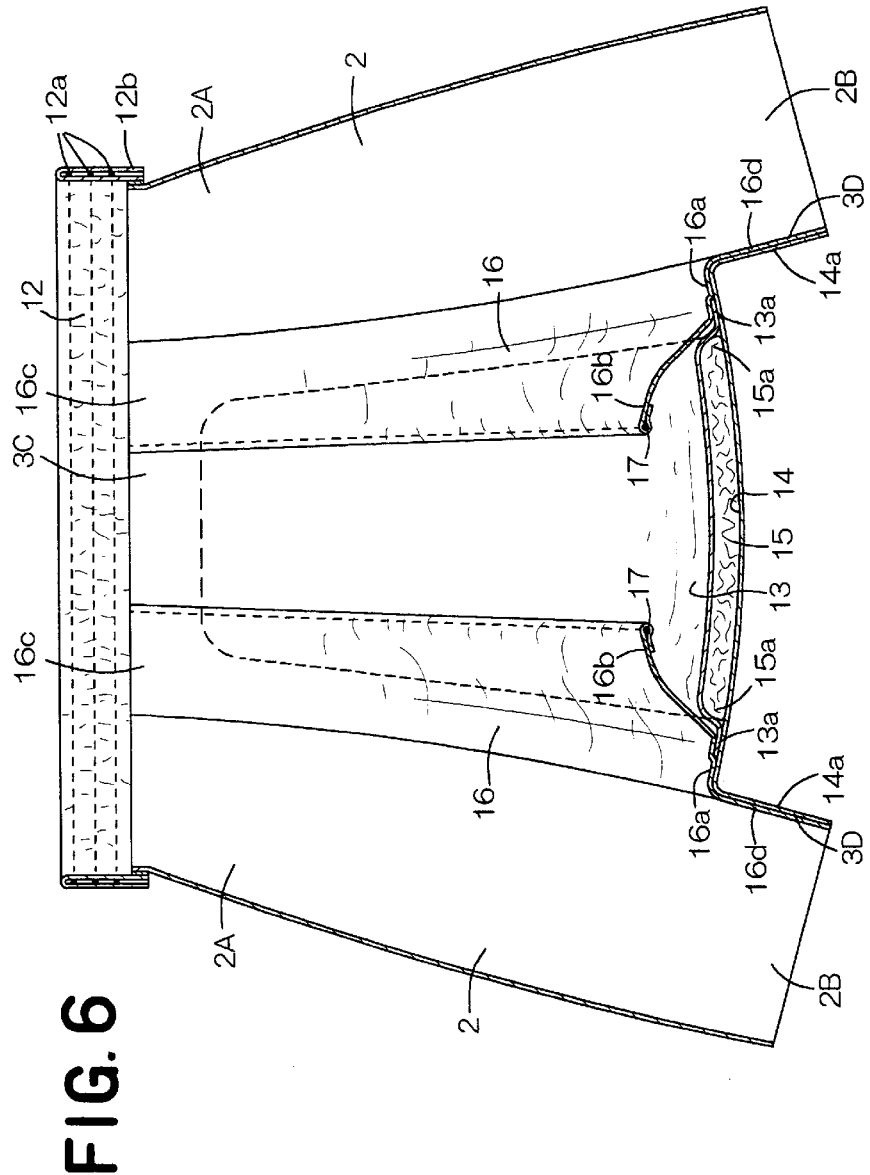
FIG. 6 is a sectional view taken along a line B—B in FIG. 5.
Figure 7:
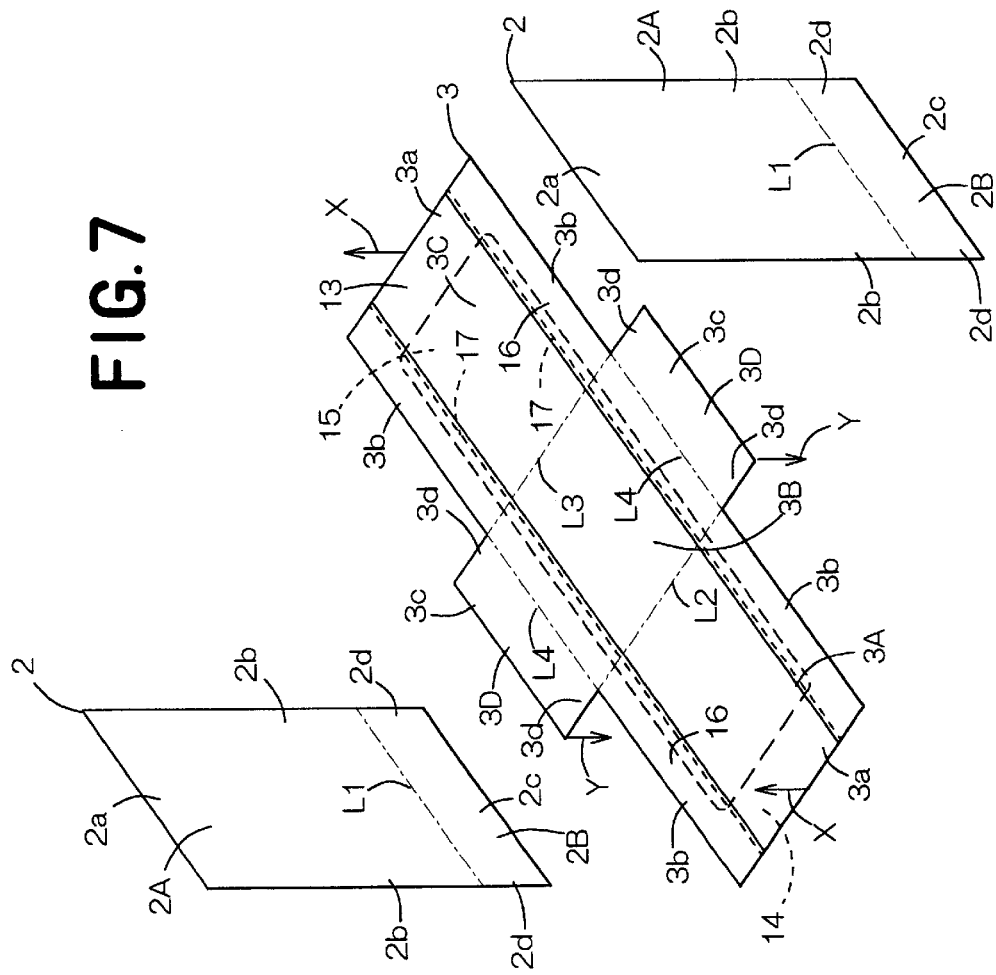
FIG. 7 is an exploded perspective view showing the pants of FIG. 5.

FIG. 5 is a view similar to FIG. 1 but showing an alternative embodiment of the pants 1 as partially broken away, FIG. 6 is a sectional view taken along a line B—B in FIG. 5 and FIG. 7 is an exploded perspective view showing the pants 1 of FIG. 5 with the elastic band being removed. Referring to FIG. 7, the single-dot-chain line L1 indicates a border line between the upper section 2A and the lower section 2B of the lateral trunk region 2, the single-dot-chain lines L2, L3 indicate border lines between the front and rear trunk sections 3A, 3C and the crotch section 3B, respectively, and the single-dot-chain line L4 indicates a border line between the crotch section 3B and the downward extension 3D.

Similarly to the pants 1 of FIG. 1, the pants 1 according to this embodiment are composed of the opposite lateral trunk regions 2 and the middle trunk region 3 and formed at its top with the waist-opening 10 provided along its peripheral edge with the elastic band 12 and formed at its bottom with a pair of the leg-openings 11. The procedure for making the pants 1 from the state illustrated by the exploded perspective view in FIG. 7 is also similar to that illustrated by FIGS. 3 and 4 and therefore is not described here.

The pants 1 of FIG. 5 is distinguished from the pants of FIG. 1 in that the middle trunk region 3 comprises a liquid-pervious topsheet 13, a liquid-impervious backsheet 14 and a liquid-absorbent core 15 disposed between these two sheets 13, 14. In the pants 1 of FIG. 5, the top- and backsheets 13, 14 are non-stretchable and the lateral trunk regions 2 are formed with a non-stretchable nonwoven fabric.

The core 15 has its entire surface covered with water-pervious tissue paper (not shown) via which the core 15 is bonded to the topsheet 13 and/or the backsheet 14. On the middle trunk region 3, a pair of side sheets 16 attached to transversely opposite side edges 15a of the core 15 so as to extend outward beyond the side edges 15a.

Each of the side sheets 16 is non-stretchable and has an outer side edge portion 16a fixed to the topsheet 13, a deformable inner side edge portion 16b extending in parallel to the outer side edge portion 16a and longitudinally opposite end portions 16c collapsed onto the inner side of the middle trunk region 3 and fixed to the topsheet 13 in this collapsed state. The outer side edge portion 16a includes a portion 16d extending outward beyond the side edge 15a of the core 15. The inner side edge portion 16b is folded back so as to wrap an elastic member 17 which is bonded under tension to the inner side edge portion 16b. The inner side edge portion 16b rises on the topsheet 13 as this elastic member 17 contracts.

In the middle trunk region 3, the transversely opposite side edges 13a of the topsheet 13 extend outward slightly beyond the transversely opposite side edges 15a of the core 15 while the transversely opposite side edges 14a of the backsheet 14 as well as the outer side edge portions 16d of the respective side sheets 16 extend further outward beyond the transversely opposite side edges 13a of the topsheet 13. The transversely opposite side edge portions 13a are disposed between the transversely opposite side edge portions 14a and the transversely opposite side edge portions 16d and fixed to the portions 14a and/or the portions 16d. The transversely opposite side edge portions 14a and the transversely opposite side edge portions 16d are put flat and bonded together.

In the vicinity of the upper edge portion 3a of the middle trunk region 3, portions of the top- and backsheets 13, 14 extending outward beyond longitudinally opposite ends of the core 15 are put flat and bonded to each other. The downward extensions 3D are formed by the side edge portions 14a of the backsheet 14 extending outward beyond the side edges 13a of the topsheet 13 and the outer side edge portions 16d of the side sheets 16.

While each of the pants 1 according to these embodiments is provided with the elastic band 12, it is also possible to attach suitable elastic members under tension directly to the respective edge portions 2a, 3a of the lateral trunk regions 2 and the middle trunk region 3.

In the case of the pants shown in FIG. 1, it is also possible to form both of the lateral trunk regions 2 and the middle trunk region 3 or at least the middle trunk region 3 with a non-stretchable nonwoven fabric. If the middle trunk region 3 is formed with a stretchable nonwoven fabric, the top- and backsheets 5, 6 and the side sheets 8, at least the backsheet 6 can be formed with a stretchable sheet.

In the case of the pants shown by FIG. 5, it is also possible to form the top- and backsheets 13, 14 and the side sheets 16 constituting the middle trunk region 3 or at least the outer sheets 14 by stretchable material and to form the lateral trunk regions 2 with a stretchable nonwoven fabric. For the pants 1 of FIG. 5, it is also possible to form the lateral trunk regions 2 with a combination of the liquid-pervious topsheet 13, the liquid-impervious backsheet 14 and the liquid-absorbent core 15 disposed between these two sheets 13, 14.

The topsheet 5, 13 may be preferably formed with a liquid-pervious hydrophilic nonwoven fabric. The backsheet 6, 14 may be preferably formed with a hydrophobic nonwoven fabric, a liquid-impervious plastic film or a laminated sheet consisting of a hydrophobic nonwoven fabric and a plastic film. The side sheets 8, 16 may be preferably formed with a hydrophobic nonwoven fabric, more preferably by breathable but a liquid-impervious nonwoven fabric.

The nonwoven fabric may be selected from a group including spunlace-, needlepunch-, meltblown-, thermalbond-, spunbond-, chemicalbond- and airthrough-types. It is also possible to use a nonwoven fabric made porous to improve a moisture-pervious property or embossed to form its sheet surface with irregularities and thereby to improve a cushioning property. Furthermore, it is also possible to use composite nonwoven fabric (SMS nonwoven fabric) consisting of melt blown nonwoven fabric having a high water-resistance sandwiched by two layers of spun bond nonwoven fabric having high strength and flexibility.

Component fiber of the nonwoven fabric may be selected from a group including polyolefine-polyester- and polyamide-based fibers and polyethylene/polypropylene or polyester conjugated fiber. Alternatively, the fiber may be added with rayon fiber or cellulose-based fiber such as cotton fiber to improve liquid absorption and/or moisture permeability of the nonwoven fabric.

The core 7, 15 comprises a mixture of fluff pulp, high absorption polymer grains and thermoplastic synthetic resin fiber compressed to a desired thickness.

Bonding of the trunk regions 2, 3, the absorbent member 4, the elastic members 9, 17, the elastic band 12, and the core 7, 15 may be carried out using suitable adhesive such as hot melt adhesive or thermal welding technique such as heat-sealing or sonic sealing.

The disposable pants of trunks-type according to this invention is characterized by a unique arrangement that the front and rear trunk sections as well as the crotch section of the middle trunk region extend so as to intersect the upper sections of the lateral trunk regions. Such arrangement advantageously enables the pants to be previously formed the space adapted to enclose belly and hip of a wearer and it has been impossible for the pants of prior art having the front and rear trunk regions placed upon each other to obtain such previously formed space. It is unnecessary for the pants according to this invention to expand the interior thereof by the wearer's belly and hip.

What is claimed is:

1. Disposable trunks-type pants, having a waist-opening and a pair of leg-openings, said pants comprising a pair of lateral trunk panels opposed to each other and a middle trunk panel extending between said lateral trunk panels; wherein
   each of the lateral trunk panels has an upper section and a lower section extending downward from said upper section;
   said middle trunk panel has a front trunk section, a rear trunk section opposed to said front trunk section, a crotch section extending between said front and rear trunk sections, and a pair of downward extensions extending downward from transversely opposite sides of said crotch section;
   each of the upper sections and the front and rear trunk sections has side edges and an upper edge, the side edges of each of the upper sections are bonded to the respective side edges of the front and rear trunk sections, the upper edges of the upper sections and the front and rear trunk sections are not bonded to each other and together define a peripheral edge of said waist-opening;
   each of the lower sections and the downward extensions has side edges and a lower edge, the side edges of each of the lower sections are bonded to the respective side edges of the downward extensions, the lower edges of the lower sections and the downward extensions are not bonded to each other and together define peripheral edges of said leg-openings; and
   the front trunk section extend continuously and seamlessly between bonding lines where the side edges of the upper sections are bonded to the respective side edges of the front trunk section.

2. The disposable trunks-type pants according to claim 1, further comprising a separate absorbent panel being adapted to absorb and to hold excretion, lying on an inner side of said middle trunk panel, and being attached at least to said crotch section;

wherein said absorbent panel comprises a liquid-pervious topsheet, a liquid-impervious backsheet and a liquid-absorbent core disposed between the topsheet and backsheet.

3. The disposable trunks-type pants of claim 2, wherein said crotch section has a width, defined by a distance between the transversely opposite sides, greater than or equal to a width of the absorbent core.

4. The disposable trunks-type pants of claim 2, wherein the backsheet is intermittently bonded to the inner side of said middle trunk panel.

5. The disposable trunks-type pants according to claim 1, wherein said middle trunk panel comprises a liquid-pervious topsheet, a liquid-impervious backsheet and a liquid-absorbent core disposed between the topsheet and backsheet.

6. The disposable trunks-type pants of claim 1, wherein the lower sections and the associated downward extensions define two abbreviated legs of said pants, said legs extending downwardly from the crotch section.

7. The disposable trunks-type pants of claim 1, wherein the lower sections and the associated downward extensions define two tubular leg structures of said pants, said leg structures extending downwardly from the crotch section.

8. The disposable trunks-type pants according to claim 7, further comprising a separate absorbent panel being adapted to absorb and to hold excretion, lying on an inner side of said middle trunk panel, and being attached at least to said crotch section;

wherein said absorbent panel comprises a liquid-pervious topsheet, a liquid-impervious backsheet and a liquid-absorbent core disposed between the topsheet and backsheet.

9. The disposable trunks-type pants according to claim 7, wherein said middle trunk panel comprises a liquid-pervious topsheet, a liquid-impervious backsheet and a liquid-absorbent core disposed between the topsheet and backsheet.

10. The disposable trunks-type pants of claim 9, wherein said crotch section has a width, defined by a distance between the transversely opposite sides, greater than or equal to a width of the absorbent core.

11. The disposable trunks-type pants of claim 9, wherein the backsheet is intermittently bonded to the inner side of said middle trunk panel.

12. Disposable trunks-type pants, having a waist-opening and a pair of leg-openings, said pants comprising a pair of lateral trunk panels opposed to each other and a middle trunk panel extending between said lateral trunk panels; wherein each of the lateral trunk panels has an upper section and a lower section extending downward from said upper section;

said middle trunk panel has a front trunk section, a rear trunk section opposed to said front trunk section, a crotch section extending between said front and rear trunk sections, and a pair of downward extensions extending downward from transversely opposite sides of said crotch section;

each of the upper sections and the front and rear trunk sections has side edges and an upper edge, the side edges of each of the upper sections are bonded to the respective side edges of the front and rear trunk sections, the upper edges of the upper sections and the front and rear trunk sections are not bonded to each other and together define a peripheral edge of said waist-opening;

each of the lower sections and the downward extensions has side edges and a lower edge, the side edges of each of the lower sections are bonded to the respective side edges of the downward extensions, the lower edges of the lower sections and the downward extensions are not bonded to each other and together define peripheral edges of said leg-openings; and each of said lateral trunk panels comprises a liquid-pervious topsheet, a liquid-impervious backsheet and a liquid-absorbent core disposed between the topsheet and backsheet.

13. Disposable trunks-type pants, having a waist-opening and a pair of leg-openings, said pants comprising a pair of lateral trunk panels opposed to each other and a middle trunk panel extending between said lateral trunk panels; wherein each of the lateral trunk panels has an upper section and a lower section extending downward from said upper section;

said middle trunk panel has a front trunk section, a rear trunk section opposed to said front trunk section, a crotch section extending between said front and rear trunk sections, and a pair of downward extensions extending downward from transversely opposite sides of said crotch section;

each of the upper sections and the front and rear trunk sections has side edges and an upper edge, the side edges of each of the upper sections are bonded to the respective side edges of the front and rear trunk sections, the upper edges of the upper sections and the front and rear trunk sections are not bonded to each other and together define a peripheral edge of said waist-opening;

each of the lower sections and the downward extensions has side edges and a lower edge, the side edges of each of the lower sections are bonded to the respective side edges of the downward extensions, the lower edges of the lower sections and the downward extensions are not bonded to each other and together define peripheral edges of said leg-openings;

the lower sections and the associated downward extensions define two tubular leg structures of said pants, said leg structures extending downwardly from the crotch section; and each of said lateral trunk panels comprises a liquid-pervious topsheet, a liquid-impervious backsheet and a liquid-absorbent core disposed between the topsheet and backsheet.

* * * * *